US006379383B1

(12) United States Patent
Palmaz et al.

(10) Patent No.: US 6,379,383 B1
(45) Date of Patent: Apr. 30, 2002

(54) ENDOLUMINAL DEVICE EXHIBITING IMPROVED ENDOTHELIALIZATION AND METHOD OF MANUFACTURE THEREOF

(75) Inventors: Julio C. Palmaz; Eugene A. Sprague; Cristina Simon; Denes Marton, all of San Antonio; Roger W. Wiseman, Bulverde; Christopher E. Banas, San Antonio, all of TX (US)

(73) Assignee: Advanced Bio Prosthetic Surfaces, Ltd., San Antonio, TX (US)

( * ) Notice: Subject to any disclaimer, the term of this patent is extended or adjusted under 35 U.S.C. 154(b) by 0 days.

(21) Appl. No.: 09/443,929

(22) Filed: Nov. 19, 1999

(51) Int. Cl.[7] .................................................. A61F 2/06
(52) U.S. Cl. ...................................................... 623/1.49
(58) Field of Search ........................... 623/1.49, 1.18, 623/1.2, 1.44, 1.45, 1.46, 1.47; 606/191, 195, 198

(56) References Cited

U.S. PATENT DOCUMENTS

| | | | |
|---|---|---|---|
| 4,510,182 A | 4/1985 | Cornils et al. | 427/427 |
| 4,751,099 A | 6/1988 | Niino et al. | 427/427 |
| 4,846,834 A | 7/1989 | von Recum et al. | 623/623 |
| 5,049,251 A | 9/1991 | Inone | 204/204 |
| 5,061,914 A | 10/1991 | Busch et al. | 337/60 |
| 5,084,151 A | 1/1992 | Vallana | 204/204 |
| 5,133,845 A | 7/1992 | Vallana et al. | 204/192 |
| 5,158,750 A | 10/1992 | Finicle | |
| 5,242,710 A | 9/1993 | Claar et al. | 427/427 |
| 5,277,933 A | 1/1994 | Claar et al. | 427/427 |
| 5,329,514 A | 7/1994 | Eguchi et al. | |
| 5,370,684 A | 12/1994 | Vallana et al. | 623/623 |
| 5,376,463 A | 12/1994 | Bak et al. | |
| 5,387,247 A | 2/1995 | Vallana et al. | 623/623 |
| 5,421,955 A | 6/1995 | Lau et al. | 216/48 |
| 5,477,864 A | 12/1995 | Davidson | 128/771 |

(List continued on next page.)

FOREIGN PATENT DOCUMENTS

| | | | |
|---|---|---|---|
| DE | 1452370 | 3/1969 | |
| EP | 0400947 | 12/1990 | |
| EP | 0442303 | 8/1991 | |
| JP | 51055724 | 5/1976 | |
| JP | 61-88135 | 5/1986 | |
| JP | 11267462 | 10/1999 | |
| WO | WO 97/07257 | 2/1997 | |
| WO | 97/44692 | 11/1997 | G02B/6/16 |
| WO | 98/13537 | 4/1998 | C25D/1/00 |
| WO | 98/45506 | 10/1998 | C25D/7/04 |
| WO | 99/23977 | 5/1999 | A61F/2/06 |
| WO | WO99/62432 | 9/1999 | A61F/2/06 |
| WO | WO 01/53559 | 7/2001 | |
| WO | WO 01/55473 | 8/2001 | |
| WO | WO 01/56502 | 8/2001 | |

OTHER PUBLICATIONS

"Liquid Sources for Chemical Vapor Deposition of Group and Metal Nitrides", by Gordon, et al., www.techtransfer.harvard.edu/cgi–bin/TALSearch.cgi'full_report=1&case=3, Case Number 1709.

"Fabrication of Small–Scale Coils and Bands as Photomasks on Optical Fibers for generation of In–Fiber Gratings, Electromagnets as Micro–NMR Coils, Microtransformers, and Intra–Vascular Stents" www.techtransfer,harvard.edu/cgi–bin/TALSearch.cgi?full_report=1&case=72, Case Number 1263.

(List continued on next page.)

Primary Examiner—Kevin Truong
(74) Attorney, Agent, or Firm—David G. Rosenbaum

(57) ABSTRACT

An implantable endoluminal device which is fabricated from materials which present a blood or body fluid and tissue contact surface which has controlled heterogeneities in material constitution. An endoluminal stent which is made of a material having controlled heterogeneities in the stent material along the blood flow surface of the stent and the method of fabricating the stent using vacuum deposition methods.

12 Claims, 2 Drawing Sheets

U.S. PATENT DOCUMENTS

| | | | |
|---|---|---|---|
| 5,514,154 A | 5/1996 | Lau et al. | 606/606 |
| 5,540,820 A | 7/1996 | Terakado et al. | 204/192.3 |
| 5,545,210 A | 8/1996 | Hess et al. | 623/623 |
| 5,569,295 A | 10/1996 | Lam | 606/606 |
| 5,593,442 A | 1/1997 | Klein | 623/623 |
| 5,603,721 A | 2/1997 | Lau et al. | 606/606 |
| 5,605,714 A | 2/1997 | Dearnaley et al. | 427/427 |
| 5,607,445 A | 3/1997 | Summers | 606/623 |
| 5,607,463 A | 3/1997 | Scwartz et al. | 623/623 |
| 5,609,629 A | 3/1997 | Fearnot et al. | 623/623 |
| 5,628,788 A | 5/1997 | Pinchuk | 623/623 |
| 5,630,840 A | 5/1997 | Mayer | 623/623 |
| 5,647,858 A | 7/1997 | Davidson et al. | 604/264 |
| 5,649,951 A | 7/1997 | Davidson | 606/198 |
| 5,656,036 A | 8/1997 | Palmaz | 623/606 |
| 5,683,453 A | 11/1997 | Palmaz | 623/623 |
| 5,685,961 A | 11/1997 | Pourrezaei et al. | 204/192 |
| 5,690,670 A | 11/1997 | Davidson | 606/198 |
| 5,723,219 A | 3/1998 | Kolluri | 428/428 |
| 5,725,573 A | 3/1998 | Dearnaley et al. | 623/427 |
| 5,728,158 A | 3/1998 | Lau et al. | 623/606 |
| 5,735,896 A | 4/1998 | Amon et al. | 623/623 |
| 5,744,515 A | 4/1998 | Clapper | 523/523 |
| 5,765,418 A | 6/1998 | Rosenberg | 72/72 |
| 5,772,864 A | 6/1998 | Moller et al. | 205/205 |
| 5,776,162 A | 7/1998 | Globerman | 606/606 |
| 5,780,807 A | 7/1998 | Saunders | 219/29 |
| 5,782,908 A | 7/1998 | Cahalan et al. | 623/623 |
| 5,782,910 A | 7/1998 | Davidson | 623/3 |
| 5,788,558 A | 8/1998 | Klein | 451/451 |
| 5,798,042 A | 8/1998 | Chu et al. | |
| 5,811,151 A | 9/1998 | Hendricks et al. | 427/427 |
| 5,824,045 A | 10/1998 | Alt | 623/606 |
| 5,824,049 A | 10/1998 | Ragheb | 623/623 |
| 5,824,056 A | 10/1998 | Rosenberg | 623/606 |
| 5,840,009 A | 11/1998 | Fischell et al. | 600/3 |
| 5,843,117 A | 12/1998 | Alt et al. | 606/623 |
| 5,843,289 A | 12/1998 | Lee et al. | 204/192 |
| 5,849,206 A | 12/1998 | Amon et al. | 216/216 |
| 5,855,600 A | 1/1999 | Alt | 623/623 |
| 5,855,802 A | 1/1999 | Acciai et al. | 216/8 |
| 5,855,955 A | 1/1999 | Claar et al. | 427/427 |
| 5,858,556 A | 1/1999 | Eckert et al. | 428/428 |
| 5,866,113 A | 2/1999 | Hendricks et al. | 424/424 |
| 5,868,782 A | 2/1999 | Frantzen | 606/606 |
| 5,873,904 A | 2/1999 | Ragheb et al. | 623/623 |
| 5,876,432 A | 3/1999 | Lau et al. | 623/623 |
| 5,879,370 A | 3/1999 | Fischell et al. | 606/623 |
| 5,891,507 A | 4/1999 | Jayaraman | 427/427 |
| 5,895,406 A | 4/1999 | Gray et al. | 606/623 |
| 5,899,935 A | 5/1999 | Ding | 623/623 |
| 5,907,893 A | 6/1999 | Zando-Azizi | 29/29 |
| 5,913,896 A | 6/1999 | Boyle et al. | 623/623 |
| 5,919,225 A | 7/1999 | Lau et al. | 623/623 |
| 5,925,063 A | 7/1999 | Khoaravi | 606/606 |
| 5,932,299 A | 8/1999 | Katoot | 427/427 |
| 5,938,682 A | 8/1999 | Hojeibane et al. | 606/623 |
| 5,938,697 A | 8/1999 | Killion et al. | 623/623 |
| 5,945,153 A | 8/1999 | Dearnaley | 427/427 |
| 5,951,881 A | 9/1999 | Rogers et al. | 216/41 |
| 5,955,588 A | 9/1999 | Tsang et al. | 536/514 |
| 5,962,138 A | 10/1999 | Kolluri et al. | 428/428 |
| 5,968,091 A | 10/1999 | Pinchuk et al. | 623/623 |
| 5,972,018 A | 10/1999 | Israel et al. | 606/623 |
| 5,972,027 A | 10/1999 | Johnson et al. | 623/623 |
| 5,984,905 A | 11/1999 | Dearnaley et al. | 604/427 |
| 6,013,855 A * | 1/2000 | McPherson et al. | 623/1.49 |
| 6,015,429 A | 1/2000 | Lau et al. | 623/623 |
| 6,019,784 A | 2/2000 | Hines | 623/600 |
| 6,022,370 A | 2/2000 | Tower | 606/606 |
| 6,027,526 A | 2/2000 | Limon et al. | 623/623 |
| 6,312,463 B1 | 2/2000 | Rourke et al. | 623/1.19 |
| 6,033,433 A | 3/2000 | Ehr et al. | 623/623 |
| 6,072,597 A | 3/2000 | Kveen et al. | 606/623 |
| 6,056,776 A | 5/2000 | Lau et al. | 623/623 |
| 6,059,808 A | 5/2000 | Boussignac | 606/606 |
| 6,066,167 A | 5/2000 | Lau et al. | 623/1 |
| 6,066,168 A | 5/2000 | Lau et al. | 623/623 |
| 6,066,169 A | 5/2000 | McGuiness | 623/1.16 |
| 6,071,305 A | 6/2000 | Brown et al. | 623/623 |
| 6,086,773 A | 7/2000 | Dufrene et al. | 216/216 |
| 6,096,175 A | 8/2000 | Roth | 204/204 |
| 6,106,642 A | 8/2000 | DiCarlo et al. | 148/148 |
| 2001/0039449 A | 1/2000 | Johnson et al. | 623/1.19 |

OTHER PUBLICATIONS

"Reactions of BiologicalCells to Nanostructures", ny Curtis, et al., AVS 46th International Symposium, Paper BI–WeM2 (Oct. 27, 1999).

"Biocompatibility of Cardiac Cells on Silane–Modified Surfaces" AVS 46th International Symposium Paper BI–WeM5 (Oct. 27, 1999).

"Biofunctionalization of Surfaces with Peptide Amphilphiles" AVS 46th International Symposium, Paper No. BI–WeM7 (Oct. 27, 1999).

"Plasma Copolymer Surfaces for Cell Culture" AVS 46th International Symposium, Paper No. Paper BI–WeM9 (Oct. 27, 1999).

"Plasama Co–polymer Surfaces for the Controlled Adsorption of Common Proteins" AVS 46th International Symposium, Paper No. BI–FrM2 (Oct. 29, 1999).

"Biofilm–Titanium Chemistry of Adhesion Using X–ray Photoelectron Spectroscopy" AVS 46th International Sumpodsium, Paper No. BI–FrM10.

"Nanoscale Pattering of Gold for Attachment of Supporteds Lipid Bilayers" AVS 46th International Symposium, Paper No. BI–FrM10.

"Focused Ion Beam NonaFabrication", Http://www/glue.umd.edu/~astan/avs04.htm.

"Amorphous Carbon and C:N Thin Films" http://www.glue.umd.edu/~astan/avs01.htm.

Multilayer Ceramic/Metallic Coatings by Ion Beam–Assisted, Electron Beam Physical Vapor (EB–PVD) Deposition, Penn State Appled Research Laboratory, pp. 1–4 (1997).

"Benefits From Diamond–Like Coated Stainless Steel Stents", http://www.phytis.com./stents0.htm, pp. 1–2.

"Adhesion of Bovine Serus Albumin on Coated DLC (Diamond–Like) ans Uncoated ($SiO_2$/$TiO_2$) Sensor Chips", http://www.phytis.com/stent4.htm, pp. 1–2.

"Flow Cytometric investigation", http://www/phytis.com/stent6.htm, pp. 1–3.

"Pre–clinical and Clinical Evaluation", http://www.phytis.com/stent2.htm, pp. 1–2.

"The New Phytis Stent", http://www.phytis.com/stent1.htm, pp. 1–2.

"Invulnerability and Resistance of DLC–Coating" , http:/www.phytis.com/stent3.htm, pp. 1–3.

"Material In Use and Its Biocompatibilty" http://www,phytis.com/stent5.htm, pp. 1–2.

"Expertise Concerning the Implementation of the Phytis Diamond As stent Performed at the Institute for Expermential Medicine (IEM)", http://www.phytis.com/stent9.htm, pp. 1.

"Phytis L.D.A. Home Page information", http://www/phytis.com/content/htm, pp. 1–15.

"Risk Analysis of Stents with a Diamond–Like Coated Surface For Use in Prosthetic Implants", http://www.phytis.com/risk.htm, pp. 1–6.

"Directions for Use, DIAMOND AS® Stent", http:/www.phytis.com/direcuse.htm, pp. 1–8.

"Stents: Literature", http://www.phytis.com/liter.htm, pp. 1–8.

"Vacuum Conditions for Sputtering Thin Film TiNi", *Journal of Vacuum Science and Technology, JVST A Online*, pp.1–2 (Abstract view).

"Oriented nickel–tetanium shape memory alloy films prepared by annealing during deposition", by Kathleen Gisser, et al., *Applied Physics Letters*, vol. 61, Issue 14, pp. 1632–1634 (Abstract view).

"Relative importance of bombardment energy and intensity in ion plating", K.S. Fancey, et al., *Journal of Vacuum Science & Technology A: Vacuum, Surfaces and Films*, vol. 13, Issue 2, pp. 428–435 (Abstract view) Mar. 1995.

"Tjhe Effecte of Ion Irradiation on NiTi Shape Memory Alloy Thin Films" by F. Goldberg and E. Knystautas, *Proceedings of the Second International Conference on Shape Memory and Superelastic Technologies Asilomar Conference Center, Pacific Grove, California, USA*, pp. 177–182 (1987).

"Constitutive Parts of a Shape Memory Alloy Titanium Nickel Thin Film Catheter" by L. Buchailot, et al., *Proceedings of the Second International Conference on Shape Memory and Superelatic Technologies Asilomar Conference Center, Pacific Grove, California, USA*, pp. 183–188 (1997).

"The Effects of HCD Technological Factors on the NiTi SMA Film Thickness" by Q. Pingshan, et al., *Proceedings of the Second International Confefence on Shape Memory and Superelastic Technologies Asilomar Conference Center, Pacific Grove, California, USA*, pp. 173–176 (1997).

"The Characteristics of NiTi HCD–Deposited SMA Films" by H. Weixin, et al., *Proceedings of the Second International Conference on Shape Memory and Superelastic Technologies Asilomar Conference Center, Pacific Grove, California, USA*, pp. 167–172 (1997).

"Microstructure of Ti–Rich TiNi Thin Films" by A. Ishida, et al., *Proceedings of the second International Conference on Shape Memory and Superelastic Technologies Asilomar Conference Center, Pacific Grove, California, USA*, pp. 161–166 (1997).

"Thin Film Shape Memory Alloy Microactuators" by TiNi Alloy Company (online).

"Progress in Thin Film Shape Memory Microactuators" by Johnson, et al., www.sma–means.com/reacent.htm (Overview), pp 1–5.

"The influence of ion irradiation during growth on the chemical stability of film/substrate systems" by W. Ensinger, *Surface and Coatings Technology*, vol. 80, pp. 35–48 (1996).

"Sputtering Target High–Quality Thin Film Materials" by AMETEK Specialty Metal Products online at www.ametek84.com/fd–sputtering.html, pp. 1–3.

"A Concise History of Vacuum Coating Technology, Part 2: 1940 to 1975" by D. Mattox, ww.svc.org/Historyof Vac2.htm, pp. 1–15.

"Model Surface for Studying and Controlling the Adhesion of Cells" by M. Mrksich, AVS $47^{th}$ International Symposium, Invited Paper No. Bl+EL=TuA1 (Oct. 3, 2000).

"Cell Response to Chemically and Topographically Modified Surfaces" by D.S. Sutherland, et al., AVS $47^{th}$ International Symposium, Paper No. Bl+EL=TuA3 (Oct. 3, 2000).

"Tissue Formation of Hepatocytes on Micro–Porous films of Polyactide" by T, Nishikawa, et al., AVS $47^{th}$ International Symposium, Paper No. Bl+EL=TuA10 (Oct. 3, 2000).

"Endothelial Cell Organization on Micropatterened Protein Surfaces" by R. Daw, et al., AVS $47^{th}$ International Symposium, Paper No. Bl–WeP21 (Oct. 4, 2000).

"The Nanomechanical Properties of Thin Films" by J.E. Houston, AVS $47^{th}$ International Symposium, Paper No. TF–TuA1 (Oct. 3, 2000).

"Anomalous Plastic and Elastic Behaviors of Sputter–deposited TiN with 10 or 20 Inserted Thin Al Layers Evaluated by Nanoidentation" by Kusano, et al., AVS $47^{th}$ International Symposium, Paper No. TF–TuA3 (Oct. 3, 2000).

"Recent Progress in the Application of Thin Film Shape Memory Alloys" by A.D. Johnson and J.D. Busch, *Proceedings of the First International Conference on Shape Memory and Superelastic Technologies Asilomar Conference Center, Pacific Grove, California, USA*, pp. 299–310 (1994).

"Shape Memory Properties in NiTl Sputter–deposited Film", by J.D. Busch and A.D. Johnson, *J Appl. Phys*, vol. 68, No. 12, pp. 6224–6226 (Dec. 15, 1990).

"Thin–film Processing of TiNi Shape Memory alloy" by J.A. Waker K.J. Gabriel, *Sensors and Actuators*, a21–A23, pp. 243–246 (1990).

"Sputter–deposited of TiNi, TiNiPd and TiPd films displaying the two–way shape–memory effect" by E. Quandt, et al., *Sensors and Actuators*, A 53, pp. 434–439 (1996).

"Applications of Shape–Memory Alloy Thin Films" A.D. Johnson and V.V. Martynov, *Proceedings of the Second International Conference on Shape Memory and Superelastic Technologies Asilomar Conference center, Pacific Grove, Californis, USA*, pp. 1–8 (1997).

"Multicomponent Film Deposition by Target Biasing", *IBM Technical Disclosure Bulletin*, pp. 1–2 (Jul. 1980).

"Thin film shape memory microvalves with adjustable operation temperature"by M. Kohl, D. Dittma, E. Quandt, B. Winzek, *Sensors and Actuators*, vol. 83, No. 1–3, (May 2000), pp. 214–219

* cited by examiner

ENDOLUMINAL DEVICE EXHIBITING IMPROVED ENDOTHELIALIZATION AND METHOD OF MANUFACTURE THEREOF

BACKGROUND OF THE INVENTION

The present invention relates generally to implantable endoluminal medical devices which contact biological fluids and tissues on at least one surface of the medical device. More particularly, the present invention relates to endoluminal stents which are implanted into anatomical passageways using minimally invasive techniques. Endoluminal stents are frequently used post-angioplasty in order to provide a structural support for a blood vessel and reduce the incidence of restenosis following percutaneous balloon angioplasty. A principal example of the present invention are endovascular stents which are introduced to a site of disease or trauma within the body's vasculature from an introductory location remote from the disease or trauma site using an introductory catheter, passed through the vasculature communicating between the remote introductory location and the disease or trauma site, and released from the introductory catheter at the disease or trauma site to maintain patentency of the blood vessel at the site of disease or trauma.

While the use of endoluminal stents has successfully decreased the rate of restenosis in angioplasty patients, it has been found that a significant restenosis rate continues to exist even with the use of endoluminal stents. It is generally believed that the post-stenting restenosis rate is due, in major part, to a failure of the endothelial layer to regrow over the stent and the incidence of smooth muscle cell-related neointimal growth on the luminal surfaces of the stent. Injury to the endothelium, the natural nonthrombogenic lining of the arterial lumen, is a significant factor contributing to restonisis at the situs of a stent. Endothelial loss exposes thrombogenic arterial wall proteins, which, along with the generally thrombogenic nature of many prosthetic materials, such as stainless steel, titanium, tantalum, Nitinol, etc. customarily used in manufacturing stents, initiates platelet deposition and activation of the coagulation cascade, which results in thrombus formation, ranging from partial covering of the luminal surface of the stent to an occlusive thrombus. Additionally, endothelial loss at the site of the stent has been implicated in the development of neointimal hyperplasia at the stent situs. Accordingly, rapid re-endothelialization of the arterial wall with concomitant endothelialization of the body fluid or blood contacting surfaces of the implanted device, is considered critical for maintaining vasculature patency and preventing low-flow thrombosis.

At present, most endoluminal stents are manufactured of stainless steel, which is known to be thrombogenic. In order to reduce the thrombogenicity of the stainless steel and to maintain sufficient dimensional profiles for catheter delivery, most stents minimize the metal surface area which contacts blood, in order to minimize thrombus formation after implantation. Thus, in order to reduce the thrombogenic response to stent implantation, as well as reduce the formation of neointimal hyperplasia, it would be advantageous to increase the rate at which endothelial cells from endothelium proximal and distal to the stent situs, migrate onto and the endothelial coverage of the luminal surface of the stent which is in contact with blood flow through the vasculature.

The surface of a solid, homogeneous material can be conceptualized as having unsaturated inter-atomic and inter-molecular bonds forming a reactive plane ready to interact with the environment. In practice, a perfectly clean surface is unattainable because of immediate adsorption of airborne species, upon exposure to ambient air, of O, $O_2$, $CO_2$, $SO_2$, NO, hydrocarbons and other more complex reactive molecules. Reaction with oxygen implies the formation of oxides on a metal surface, a self-limiting process, known as passivation. An oxidized surface is also reactive with air, by adsorbing simple, organic airborne compounds. Assuming the existence of bulk material of homogeneous subsurface and surface composition, oxygen and hydrocarbons may adsorb homogeneously. Therefore, further exposure to another environment, such as the vascular compartment, may be followed by a uniform biological response.

Current metallic vascular devices, such as stents, are made from bulk metals made by conventional methods, and stent precursors, such as hypotubes, are made with many steps each of which introduce processing aides to the metals. For example, olefins trapped by cold drawing and transformed into carbides or elemental carbon deposit by heat treatment, typically yield large carbon rich areas in 316L stainless steel tubing manufactured by cold drawing process. The conventional stents have marked surface and subsurface heterogeneity resulting from manufacturing processes (friction material transfer from tooling, inclusion of lubricants, chemical segregation from heat treatments). This results in formation of surface and subsurface inclusions with chemical composition and, therefore, reactivity different from the bulk material. Oxidation, organic contamination, water and electrolytic interaction, protein adsorption and cellular interaction may, therefore, be altered on the surface of such inclusion spots. Unpredictable distribution of inclusions such as those mentioned above provide an unpredictable and uncontrolled heterogeneous surface available for interaction with plasma proteins and cells. Specifically, these inclusions interrupt the regular distribution pattern of surface free energy and electrostatic charges on the metal surface that determine the nature and extent of plasma protein interaction. Plasma proteins deposit nonspecifically on surfaces according to their relative affinity for polar or non-polar areas and their concentration in blood. A replacement process known as the Vroman effect, Vroman L. *The importance of surfaces in contact phase reactions Seminars of Thrombosis and Hemostasis* 1987;13(1):79–85, determines a time-dependent sequential replacement of predominant proteins at an artificial surface, starting with albumin, following with IgG, fibrinogen and ending with high molecular weigh kininogen. Despite this variability, some of the adsorbed proteins have receptors available for cell attachment and therefore constitute adhesive sites. Examples are: fibrinogen glycoprotein receptor IIbIIIa for platelets and fibronectin RGD sequence for many blood activated cells. Since the coverage of an artificial surface with endothelial cells is a favorable end-point in the healing process, to favor endothelialization is desirable in implantable vascular device manufacture.

Normally, endothelial cells (EC) migrate and proliferate to cover denuded areas until confluence is achieved. Migration, quantitatively more important than proliferation, proceeds under normal blood flow roughly at a rate of 25 $\mu$m/hr or 2.5 times the diameter of an EC, which is nominally 10 $\mu$m. EC migrate by a rolling motion of the cell membrane, coordinated by a complex system of intracellular filaments attached to clusters of cell membrane attachment, integrin receptors, specifically focal contact points. The integrins within the focal contact sites are expressed according to complex signaling mechanisms and eventually couple to specific amino acid sequences in substrate adhesion molecules (such as RGD, mentioned above). An EC has roughly 16–22% of its cell surface represented by integrin clusters Davies P. F., Robotewskyi A., Griem M. L. *Endothelial cell adhesion in real time. J. Clin. Invest.* 1993;91:2640–2652, Davies, P. F., Robotewski, A., Griem, M. L., *Qualitiative studies of endothelial cell adhesion, J.Clin.Invest.*1994;93:2031–2038. This is a dynamic process, which implies more than 50% remodeling in 30 minutes. The focal adhesion contacts vary in size and distribution, but 80% of them measure less than 6 $\mu$m$^2$, with the majority of them being about 1 $\mu$m$^2$, and tend to elongate in the direction of flow and concentrate at leading edges of the cell. Although the process of recognition and signaling to determine specific attachment receptor response to attachment sites is incompletely understood, regular availability of attachment sites, more likely than not, would favorably influence attachment and migration. Irregular or unpredictable distribution of attachment sites, that might occur as a result of various inclusions, with spacing equal or smaller to one whole cell length, is likely to determine alternating hostile and favorable attachment conditions along the path of a migrating cell. These conditions may vary from optimal attachment force and migration speed to insufficient holding strength to sustain attachment, resulting in cell slough under arterial flow conditions. Due to present manufacturing processes, current implantable vascular devices exhibit such variability in surface composition as determined by surface sensitive techniques such as atomic force microscopy, X-ray photoelectron spectroscopy and time of flight secondary ion-mass spectroscopy.

There have been numerous attempts to increase endothelialization of implanted stents, including covering the stent with a polymeric material (U.S. Pat. No. 5,897,911), imparting a diamond-like carbon coating onto the stent (U.S. Pat. No. 5,725,573), covalently binding hydrophobic moieties to a heparin molecule (U.S. Pat. No. 5,955,588), coating a stent with a layer of blue to black zirconium oxide or zirconium nitride (U.S. Pat. No. 5,649,951), coating a stent with a layer of turbostratic carbon (U.S. Pat. No. 5,387,247), coating the tissue-contacting surface of a stent with a thin layer of a Group VB metal (U.S. Pat. No. 5,607,463), imparting a porous coating of titanium or of a titanium alloy, such as Ti—Nb—Zr alloy, onto the surface of a stent (U.S. Pat. No. 5,690,670), coating the stent, under ultrasonic conditions, with a synthetic or biological, active or inactive agent, such as heparin, endothelium derived growth factor, vascular growth factors, silicone, polyurethane, or polytetrafluoroethylene, U.S. Pat. No. 5,891,507), coating a stent with a silane compound with vinyl functionality, then forming a graft polymer by polymerization with the vinyl groups of the silane compound (U.S. Pat. No. 5,782,908), grafting monomers, oligomers or polymers onto the surface of a stent using infrared radiation, microwave radiation or high voltage polymerization to impart the property of the monomer, oligomer or polymer to the stent (U.S. Pat. No. 5,932,299). Thus, the problems of thrombogenicity and re-endothelialization associated with stents have been addressed by the art in various manners which cover the stent with either a biologically active or an inactive covering which is less thrombogenic than the stent material and/or which has an increase capacity for promoting re-endothelialization of the stent situs. These solutions, however, all require the use of existing stents as substrates for surface derivatization or modification, and each of the solutions result in a biased or laminate structure built upon the stent substrate. These prior art coated stents are susceptible to delamination and/or cracking of the coating when mechanical stresses of transluminal catheter delivery and/or radial expansion in vivo. Moreover, because these prior art stents employ coatings applied to stents fabricated in accordance with conventional stent formation techniques, e.g., cold-forming metals, the underlying stent substrate is characterized by uncontrolled heterogeneities on the surface thereof. Thus, coatings merely are laid upon the heterogeneous stent surface, and inherently conform to the heterogeneities in the the stent surface and mirror these heterogeneities at the blood contact surface of the resulting coating. This is conceptually similar to adding a coat of fresh paint over an old coating of blistered paint, the fresh coating will conform to the blistering and eventually, itself, blister and delaminate from the underlying substrate.

The current invention entails creating materials specifically designed for manufacture of stents and other intravascular devices. Manufacture of stents and other intravascular devices is controlled to attain a regular, homogeneous atomic and molecular pattern of distribution along their surface. This avoids the marked variations in surface composition, would create a predictable oxidation and organic adsorption pattern and would have a predictable interaction with water, electrolytes, proteins and cells. Particularly, EC migration would be supported by a homogeneous distribution of binding domains which serve as natural or implanted cell attachment sites, in order to promote unimpeded migration and attachment. Based on observed EC attachment mechanisms such binding domains should have a repeating pattern along the blood contact surface of no less than 1 $\mu$m radius and 2 $\mu$m border to border spacing between binding domains. Ideally, the inter-binding domain spacing is less than the nominal diameter of an endothelial cell in order to ensure that at any given time, a portion of an endothelial cell is in proximity to a binding domain.

SUMMARY OF THE INVENTION

In accordance with the present invention, there is provided an implantable endoluminal device which is fabricated from materials which present a blood contact surface which is substantially homogeneous in material constitution. More particularly, the present invention provides an endoluminal stent which is made of a material having controlled heterogeneities along the blood flow surface of the stent. The heterogeneities which are controlled in the present invention include: grain size, grain phase, grain material composition, stent-material composition, and surface topography at the blood flow surface of the stent. Additionally, the present invention provides methods of making an endoluminal stent having controlled heterogeneities in the stent material along the blood flow surface of the stent.

DETAILED DESCRIPTION OF THE PREFERRED EMBODIMENTS

Figure 1:
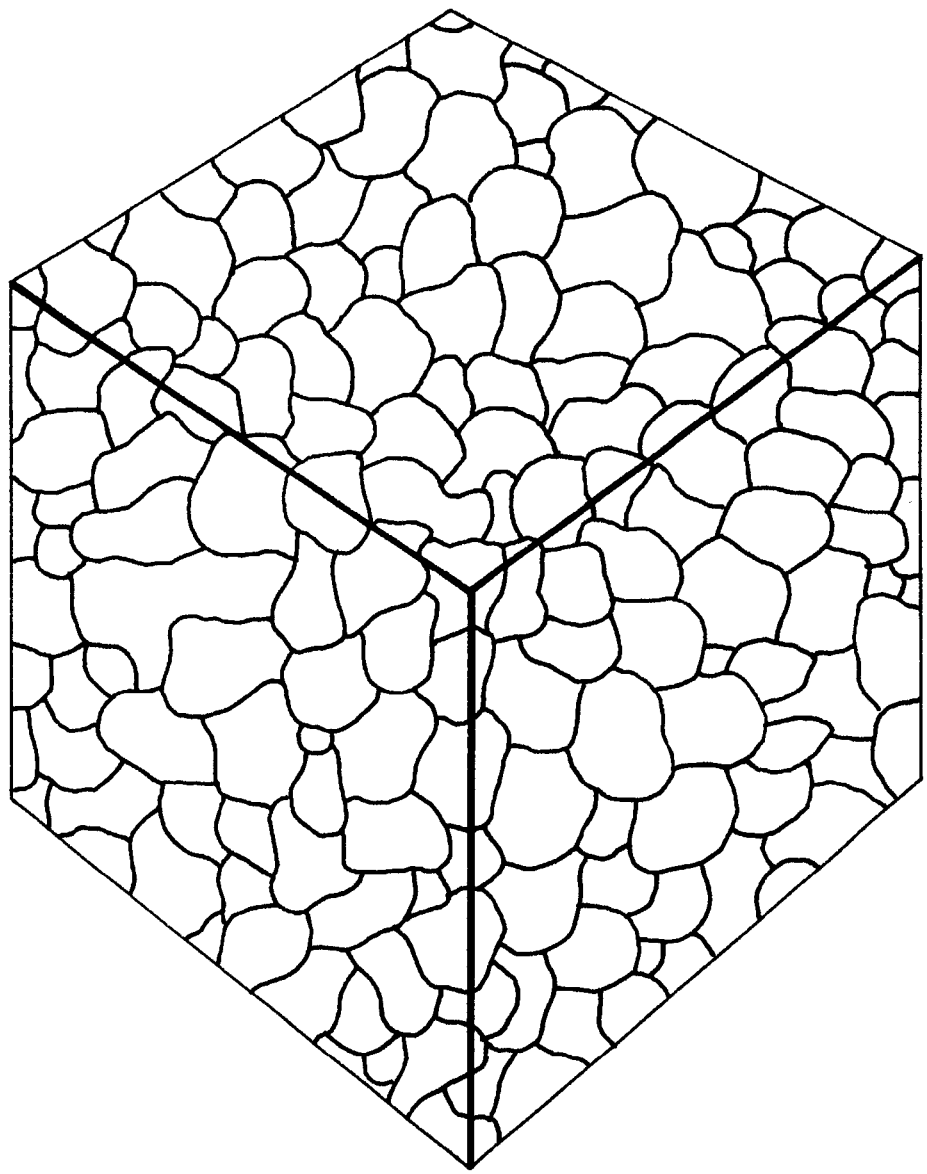
FIG. 1 is a diagrammatic representation of controlled heterogeneities in the inventive stent.
Figure 2:
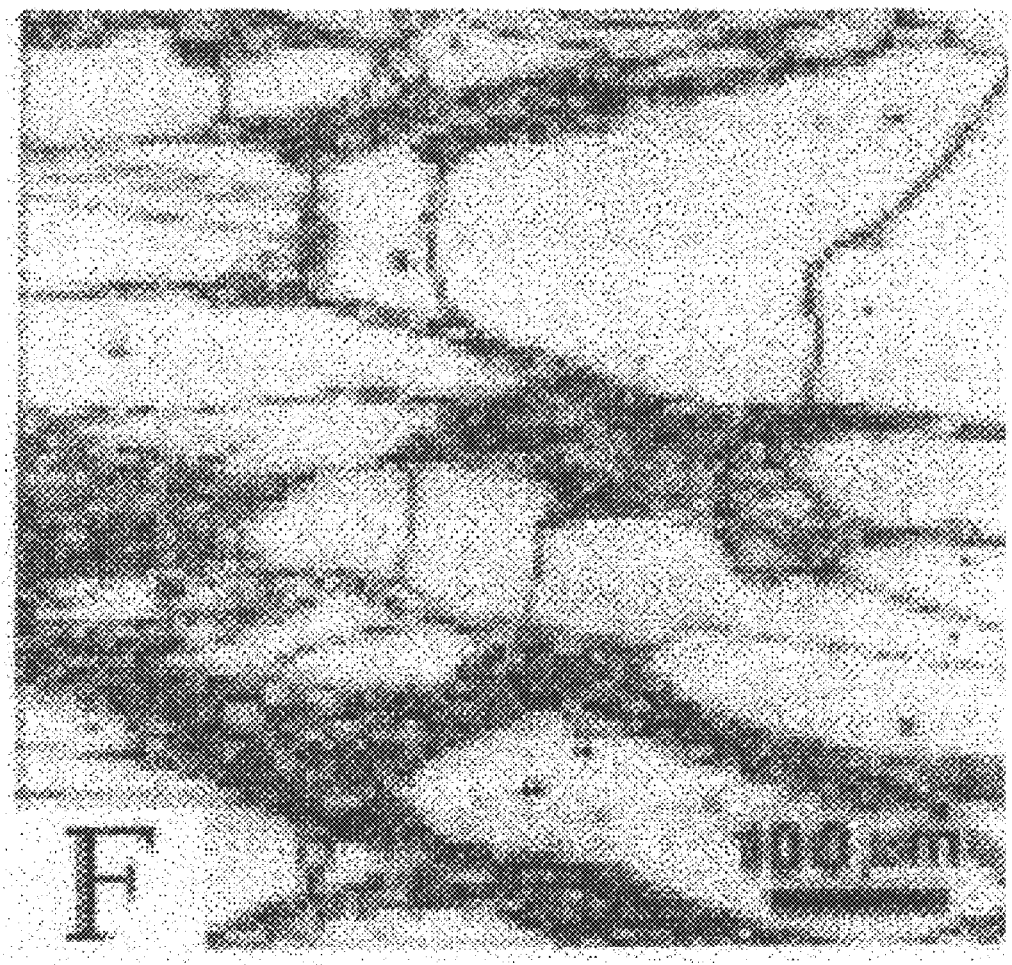
FIG. 2 is a micrograph of uncontrolled heterogeneities present in prior art stent material.

Blood protein interaction with surfaces of endoluminal devices appears to be an initial step in a chain of events leading to tissue incorporation of the endovascular device. The present invention is based, in part, upon the relationship between surface energy of the material used to make the endoluminal device and protein adsorption at the surface of the endoluminal device. The present inventors have found that a relationship exists between surface free energy and protein adsorption on metals commonly used in fabrication of endoluminal devices. In addition, specific electrostatic forces resident on the surface of metal endoluminal stents have been found to influence blood interactions with the stent surface and the vascular wall.

In accordance with the present invention there is provided a stent which is fabricated of a material having substantially homogeneous surface properties, specifically surface energy and electrostatic charge, across the blood contact surface of the stent. Current manufacturing methods for fabricating endoluminal stents fail to achieve the desired material properties of the present invention. As discussed above, stents are fabricated from bulk metals which are processed in a manner which introduces processing aides to the metal. Presently, stents are made from hypotubes formed from the bulk metals, by machining a series of slots or patterns into the hyptotube to accommodate radial expansion into a stainless steel metal tube, or by weaving wires into a mesh pattern. According to the present invention, a stent with a substantially homogeneous metal constitution, exhibiting substantially homogeneous surface properties is made by imparting a stent pattern, suitable for making either a balloon expandable or self expanding stent, onto a substrate and depositing stent-forming metal onto the stent pattern by a deposition methodology which yields a metal having controlled heterogeneities. Suitable deposition methodologies, as are known in the microelectronic and vacuum coating fabrication arts and incorporated herein by reference, are plasma deposition and physical vapor deposition which are utilized to impart a metal layer onto the stent pattern.

The present invention consists of a stent made of a bulk material, having controlled heterogeneities on the luminal surface thereof. Heterogeneities are controlled by fabricating the bulk material of the stent to have defined grain sizes which yield areas or sites along the surface of the stent having optimal protein binding capability. The characteristically desirable properties of the inventive stent are: (a) optimum mechanical properties consistent with or exceeding regulatory approval criteria, (b) minimization of defects, such as cracking or pin hole defects, (c) a fatigue life of 400 MM cycles as measured by simulated accelerated testing, (d) corrosion resistance, (e) biocompatibility without having biologically significant impurities in the material, (f) a substantially non-frictional abluminal surface to facilitate atraumatic vascular crossing and tracking and compatible with transcatheter techniques for stent introduction, (g) radiopaque at selected sites and MRI compatible, (h) have an luminal surface which is optimized for surface energy and microtopography, (i) minimal manufacturing and material cost consistent with achieving the desired material properties, and (j) high process yields.

In accordance with the present invention, the foregoing properties are achieved by fabricating a stent by the same metal deposition methodologies as are used and standard in the microelectronics and nano-fabrication vacuum coating arts, and which are hereby incorporated by reference. In accordance with the present invention, the preferred deposition methodologies include ion-beam assisted evaporative deposition and sputtering techniques. In ion beam-assisted evaporative deposition it is preferable to employ dual and simultaneous thermal electron beam evaporation with simultaneous ion bombardment of the substrate using an inert gas, such as argon, xenon, nitrogen or neon. Bombardment with an inert gas, such as argon ions serves to reduce void content by increasing the atomic packing density in the deposited material during deposition. The reduced void content in the deposited material allows the mechanical properties of that deposited material to be similar to the bulk material properties. Deposition rates up to 20 nm/sec are achievable using ion beam-assisted evaporative deposition techniques.

When sputtering techniques are employed, a 200 micron thick stainless steel film may be deposited within about four hours of deposition time. With the sputtering technique, it is preferable to employ a cylindrical sputtering target, a single circumferential source which concentrically surrounds the substrate which is held in a coaxial position within the source. Alternate deposition processes which may be employed to form the stent in accordance with the present invention are cathodic arc, laser ablation, and direct ion beam deposition. When employing vacuum deposition methodologies, the crystalline structure of the deposited film affects the mechanical properties of the deposited film. These mechanical properties of the deposited film may be modified by post-process treatment, such as by, for example, annealing, high pressure treatment or gas quenching.

Materials to make the inventive stents are chosen for their biocompatibility, mechanical properties, i.e., tensile strength, yield strength, and their ease of deposition include the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

During deposition, the chamber pressure, the deposition pressure and the partial pressure of the process gases are controlled to optimize deposition of the desired species onto the substrate. As is known in the microelectronic fabrication, nano-fabrication and vacuum coating arts, both the reactive and non-reactive gases are controlled and the inert or non-reactive gaseous species introduced into the deposition chamber are typically argon and nitrogen. The substrate may be either stationary or moveable, either rotated about its longitudinal axis, or moved in an X-Y plane within the reactor to facilitate deposition or patterning of the deposited material onto the substrate. The deposited material maybe deposited either as a uniform solid film onto the substrate, or patterned by (a) imparting either a positive or negative pattern onto the substrate, such as by etching or photolithography techniques applied to the substrate surface to create a positive or negative image of the desired pattern or (b) using a mask or set of masks which are either stationary or moveable relative to the substrate to define the pattern applied to the substrate. Patterning may be employed to achieve complex finished geometries of the resultant stent, both in the context of spatial orientation of the pattern as well as the material thickness at different regions of the deposited film, such as by varying the wall thickness of the material over its length to thicken sections at proximal and distal ends of the stent to prevent flaring of the stent ends upon radial expansion of the stent.

The stent may be removed from the substrate after stent formation by any of a variety of methods. For example, the substrate may be removed by chemical means, such as etching or dissolution, by ablation, by machining or by ultrasonic energy. Alternatively, a sacrificial layer of a material, such as carbon or aluminum, may be deposited intermediate the substrate and the stent and the sacrificial layer removed by melting, chemical means, ablation, machining or other suitable means to free the stent from the substrate.

The resulting stent may then be subjected to post-deposition processing to modify the crystalline structure, such as by annealing, or to modify the surface topography, such as by etching to affect and control the heterogeneities on the blood flow surface of the stent.

EXAMPLE 1

Stent Formation by Sputtering

A ceramic cylindrical substrate is introduced into a deposition chamber with capabilities of glow discharge substrate cleaning and sputter deposition of carbon and stainless steel. The deposition chamber is evacuated to a pressure less than or equal to $2\times10^{-7}$ Torr. Pre-cleaning of the substrate is conducted under vacuum by glow discharge. The substrate temperature is controlled to achieve a temperature between about 300 and 1100 degrees Centigrade. A bias voltage between –1000 and +1000 volts is applied to the substrate sufficient to cause energetic species arriving at the surface of the substrate to have a hyperthermal energy between 0.1 eV and about 700 eV, preferably between 5–50 eV. The deposition sources are circumferential and are oriented to deposit from the target circumferentially about the substrate.

During deposition, the deposition pressure is maintained between 0.1 and 10 mTorr. A sacrificial carbon layer of substantially uniform thickness (±5%) between 10 and 500 Angstroms is deposited circumferentially on the substrate. After depositing the carbon layer, a cylindrical film of stainless steel is deposited onto the sacrificial carbon layer on the cylindrical substrate at a deposition rate between about 10 to 100 microns/hour. After formation of the stainless steel film, the substrate is removed from the deposition chamber and heated to volatilize the intermediate sacrificial carbon layer between the substrate and the film. After removing the carbon intermediate layer, the stainless steel film is removed from the substrate and exhibits material properties similar to the bulk stainless steel target and surface properties characterized by controlled heterogeneities in grain size, material composition and surface topography. A series of patterns are then machined into the resultant stainless steel film to form a stent by electrical discharge machining (EDM) or laser cutting the film.

EXAMPLE 2

Stent Formation by Sputtering

The same operating conditions are followed as in Example 1, except that the substrate is tubular and selected to have a coefficient of thermal expansion different than that of the resultant stent. No intermediate layer of sacrificial carbon is deposited onto the substrate, and the outer surface of the substrate is etched with a pattern of recesses defining a desired stent pattern. The substrate is mounted onto a rotational jig within the deposition chamber and rotated at a uniform rate during deposition. Tantalum is used as the target material and deposited into the recesses of the substrate from a single stationary source. After deposition, the temperature of the substrate and the deposited stent are controlled to impart diametric differential in the substrate and stent and permit removal of the stent from the substrate.

EXAMPLE 3

Stent Formation by Ion Beam-assisted Evaporative Deposition

A cylindrical substrate is introduced into a deposition chamber which has capabilities of: substrate rotation and precise positioning, glow discharge substrate cleaning, ion beam-assisted evaporative deposition, and cylindrical magnetron sputtering. The deposition sources are (a) dual electron beam evaporative sources placed adjacent one another at the base of the deposition chamber at a fixed distance from the substrate, these are used with simultaneous argon ion impingement onto the substrate from a controlled ion beam source, and (b) a cylindrical magnetron sputtering source with a carbon target capable of circumferentially coating a carbon sacrificial layer of substantially uniform thickness of between 10 and 200 Angstroms onto the substrate.

The substrate temperature is controlled to achieve a substrate temperature between about 300 and 1100 degrees Centigrade. The deposition chamber is evacuated to a pressure less than or equal to $2\times10^{-7}$ Torr. A pre-cleaning of the substrate is conducted under vacuum by glow discharge. The substrate is rotated to ensure uniform cleaning and subsequent uniform deposition thickness. After cleaning the substrate is moved into the magnetron and coated with the carbon layer. The substrate is then moved into position to receive the stent-forming metal coating with simultaneous ion bombardment. One electron beam evaporation source contains titanium while the other source contains nickel. The evaporation rates of each of the titanium and nickel evaporation sources are separately controlled to form a nitinol alloy on the substrate as the stent-forming metal.

EXAMPLE 4

Planar Deposition of Stent

The same operating conditions of Example 3 are followed, except that a planar substrate is used. The deposition source is a single electron beam evaporation source containing platinum and is used with simultaneous argon ion impingement onto the substrate from a controlled ion beam source.

The substrate temperature is controlled to achieve a substrate temperature between about 300 and 1100 degrees Centigrade. The deposition chamber is evacuated to a pressure less than or equal to $2\times10^{-7}$ Torr. A pre-cleaning of the substrate is conducted under vacuum by glow discharge. After cleaning the substrate is moved into position within the deposition chamber and coated with platinum from the electron beam evaporation source with simultaneous argon ion bombardment, with the electron beam evaporation source passing platinum through a pattern mask corresponding to a stent pattern which is interposed between the source and the substrate to pass a pattern of platinum onto the substrate.

After deposition, the patterned stent is removed from the substrate and rolled about a forming substrate to a cylindrical shape and opposing ends of the planar stent material are brought into juxtaposition with one another and may be attached by laser welding or left uncoupled.

While the invention has been described with reference to its preferred embodiments, those of ordinary skill in the relevant arts will understand and appreciate that the present invention is not limited to the recited preferred embodiments, but that various modifications in material selection, deposition methodology, manner of controlling the material heterogeneities of the deposited stent material, and deposition process parameters may be employed without departing from the invention, which is to be limited only by the claims appended hereto.

What is claimed is:

1. An endoluminal stent capable of radially expanding from a first diameter to a second diameter, comprising a tubular member having luminal and abluminal surfaces thereof, at least the luminal surface having controlled heterogeneities thereupon.

2. The endoluminal stent according to claim 1, wherein the stent is made of a material selected from the group consisting of elemental titanium, vanadium, aluminum, nickel, tantalum, zirconium, chromium, silver, gold, silicon, magnesium, niobium, scandium, platinum, cobalt, palladium, manganese, molybdenum and alloys thereof, and nitinol and stainless steel.

3. The endoluminal stent according to claim 1, wherein the controlled heterogeneities are selected from the group consisting of grain size, grain phase, grain material composition, stent material composition and surface topography.

4. The endoluminal stent according to claim 1, wherein the controlled heterogeneities define polar and non-polar binding sites for binding blood plasma proteins.

5. The endoluminal stent according to claim 1, wherein the controlled heterogeneities are dimensioned to have a blood contact surface area substantially similar in size as endothelial cell surface integrin clusters.

6. The endoluminal stent according to claim 1, wherein the controlled heterogeneities define cell-adhesion domains having interdomain boundaries less than the surface area of a human endothelial cell.

7. The endoluminal stent according to claim 1, wherein the controlled heterogeneities are dimensioned to have a blood contact surface area of about less than 6 $\mu m^2$.

8. The endoluminal stent according to claim 1, wherein the controlled heterogeneity is selected from the group consisting of grain size, grain phase and grain composition.

9. The endoluminal stent according to claim 1, wherein the controlled heterogeneity is material composition.

10. The endoluminal stent according to claim 1, wherein the controlled heterogeneity is luminal surface topography.

11. The endoluminal stent according to claim 1 wherein the controlled heterogeneity has a blood contact surface less than or equal to about 10 $\mu m$ and an inter-heterogeneity boundary between about 0 and 2 $\mu m$.

12. An endoluminal stent capable of radially expanding from a first diameter to a second diameter, comprising a tubular member, having luminal and abluminal surfaces thereof, fabricated from a bulk material which forms the luminal and abluminal surfaces of the tubular member, at least the luminal surface of the bulk material having controlled heterogeneities thereupon.

* * * * *

UNITED STATES PATENT AND TRADEMARK OFFICE
CERTIFICATE OF CORRECTION

PATENT NO. : 6,379,383 B1
DATED : April 30, 2002
INVENTOR(S) : Julio C. Palmaz et al.

It is certified that error appears in the above-identified patent and that said Letters Patent is hereby corrected as shown below:

<u>Title page,</u>
Item [56], References Cited, U.S. PATENT DOCUMENTS, delete "5,776,162" and insert -- 5,776,161 --.
Delete "5,782,908" and insert -- 5,728,908 --.
Delete "6,072,597" and insert -- 6,042,597 --.

OTHER PUBLICATIONS: insert after "Group" -- 6 Metals --.
Delete "www.tech-transfer.harvard.edu/cgi-bin/TALSearch.cgi'full_report=1&case=3" and insert -- www.techtransfer.harvard.edu/cgi-bin/TALSearch.cgi?full_report=1&case=3 --.
Delete "www.techtransfer,harvard.edu/cgi-bin/TALSearch.cgi?full_report=1&case=72" and insert -- www.techtransfer.harvard.edu/cgi-bin/TALSearch.cgi?full_report=1&case=72 --.
Insert space between "Biological" and "Cells".
Delete "ny" and insert -- by --.
Delete "Sumpodsium" and insert -- Symposium --.
Delete "Supporteds" and insert -- Supported --.
Delete "www/glue.umd.edu/~astan/avs04.htm" and insert
-- www.glue.umd.edu/~astan/avs04.htm --.
Delete "ans" and insert -- and --.
Delete "http://www,phytis.com/stent5htm" and insert -- http://www.phytis.com/stent5htm --.
Delete "-" between "www" and ".".
Delete "The Effecte" and insert -- The Effects -- and replace "1987" with -- 1997 --.
Delete "Effects" and insert -- Effect -- and replace "Confefence" with
-- Conference --.
Delete "reacent.htm" and insert -- recent.htm --.
Insert -- film -- between "during" and "growth".
Insert -- s -- between "High" and "hyphen".
Replace "Surface" with -- Surfaces --.

UNITED STATES PATENT AND TRADEMARK OFFICE
CERTIFICATE OF CORRECTION

PATENT NO.   : 6,379,383 B1
DATED        : April 30, 2002
INVENTOR(S)  : Julio C. Palmaz et al.

It is certified that error appears in the above-identified patent and that said Letters Patent is hereby corrected as shown below:

OTHER PUBLICATIONS cont'd,
Delete "=" and insert -- hyphen --.
Delete "Micropatterened" and insert -- Micropatterned --.
Replace "a21" with -- A21 --.
Replace "deposited" with -- deposition --.
Insert -- by -- between "Films"" and "A.D.".
Replace "center" with -- Center --.
Delete "Californis" and insert -- California --.

Signed and Sealed this

Eleventh Day of March, 2003

JAMES E. ROGAN
*Director of the United States Patent and Trademark Office*